United States Patent
Clark et al.

(10) Patent No.: US 10,441,247 B2
(45) Date of Patent: Oct. 15, 2019

(54) HIGH VOLUME MANUFACTURE OF SINGLE ELEMENT ULTRASOUND TRANSDUCERS

(71) Applicant: KONINKLIJKE PHILIPS N.V., Eindhoven (NL)

(72) Inventors: Dennis Dean Clark, Lewistown, PA (US); Barry Carl Scheirer, McAlisterville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 766 days.

(21) Appl. No.: 15/031,755

(22) PCT Filed: Oct. 29, 2014

(86) PCT No.: PCT/IB2014/065691
§ 371 (c)(1),
(2) Date: Apr. 25, 2016

(87) PCT Pub. No.: WO2015/063702
PCT Pub. Date: May 7, 2015

(65) Prior Publication Data
US 2016/0262724 A1    Sep. 15, 2016

Related U.S. Application Data

(60) Provisional application No. 61/899,322, filed on Nov. 4, 2013.

(51) Int. Cl.
*H01L 41/107* (2006.01)
*H01L 41/047* (2006.01)
(Continued)

(52) U.S. Cl.
CPC .......... *A61B 8/4483* (2013.01); *A61B 8/4272* (2013.01); *B06B 1/0644* (2013.01)

(58) Field of Classification Search
CPC ... A61B 8/4483; A61B 8/4272; B06B 1/0644; H01L 41/107
(Continued)

(56) References Cited

U.S. PATENT DOCUMENTS 5,176,140 A    1/1993   Kami
5,493,541 A    2/1996   Snyder
(Continued)

FOREIGN PATENT DOCUMENTS

JP    H03162839 A    7/1991
JP    2001054194 A    2/2001
(Continued)

*Primary Examiner* — Thomas M Dougherty

(57) ABSTRACT

A single element ultrasound transducer is fabricated from a laminate plate which produces multiple transducer elements simultaneously. The laminate plate includes the piezo ceramic, matching layer, and backing layer with rear electrode. The laminate plate is diced while mounted on nitto tape to retain the individual elements in position after dicing. The sides of the elements are covered with an insulating coating, which permits the transducer elements to be surface mounted on flex circuit by bonding the rear electrode to a signal conductor of the flex circuit and the matching layer to a return conductor by metallically coating the mounted transducer element and return conductor on the flex circuit.

15 Claims, 4 Drawing Sheets

(51) Int. Cl.
*A61B 8/00* (2006.01)
*B06B 1/06* (2006.01)

(58) Field of Classification Search
USPC .................. 310/322, 334, 340, 365
See application file for complete search history.

(56) References Cited

U.S. PATENT DOCUMENTS

| | | | |
|---|---|---|---|
| 5,706,820 A | 1/1998 | Hossack | |
| 5,711,058 A | 1/1998 | Frey | |
| 5,884,627 A * | 3/1999 | Wakabayashi | A61B 8/12 600/447 |
| 2002/0007118 A1* | 1/2002 | Adachi | B06B 1/0611 600/443 |
| 2003/0173870 A1* | 9/2003 | Simon Hsu | B06B 1/0611 310/334 |
| 2008/0252172 A1 | 10/2008 | Yetter et al. | |
| 2009/0085440 A1* | 4/2009 | Nakamura | B06B 1/0622 310/334 |
| 2009/0183350 A1 | 7/2009 | Wulf | |
| 2011/0121687 A1 | 5/2011 | Aoki | |
| 2012/0206014 A1* | 8/2012 | Bibl | B06B 1/0644 310/331 |
| 2013/0257226 A1 | 10/2013 | Nobles | |
| 2013/0302213 A1* | 11/2013 | Lipkens | B01D 43/00 422/119 |
| 2013/0303920 A1* | 11/2013 | Corl | A61B 8/12 600/468 |
| 2014/0377834 A1* | 12/2014 | Presz, Jr. | C12M 47/02 435/173.9 |
| 2016/0231289 A1* | 8/2016 | Laudermilch | B06B 1/0622 |

FOREIGN PATENT DOCUMENTS

| | | |
|---|---|---|
| JP | 2008509774 A | 4/2008 |
| JP | 2010181355 A | 8/2010 |
| JP | 2013102399 A | 5/2013 |
| WO | 8905199 A1 | 6/1989 |
| WO | 2006018805 A1 | 2/2006 |
| WO | 2011146138 A2 | 11/2011 |
| WO | 2013001448 A1 | 1/2013 |

* cited by examiner

US 10,441,247 B2

HIGH VOLUME MANUFACTURE OF SINGLE ELEMENT ULTRASOUND TRANSDUCERS

This application is the U.S. National Phase application under 35 U.S.C. § 371 of International Application No. PCT/IB2014/065691, filed on Oct. 29, 2014, which claims the benefit of U.S. Provisional Application No. 61/899,322 filed Nov. 4, 2013. These applications are hereby incorporated by reference herein.

This invention relates to acoustic transducers and, in particular, to single element ultrasound transducers.

Single element transducers for an ultrasound system transmit acoustic ultrasonic energy from an emitting (front) face of the transducer element and/or receive ultrasonic energy and convert it into electrical signals for processing. Single element transducers can be distinguished from array transducers, which operate by timed transmission and reception of ultrasound from a plurality of elements simultaneously. Traditionally, single element transducers have been produced by creating a round piece of piezo ceramic with electrodes plated on its front and rear surfaces. The disc-like element is placed into a cylindrical housing. The front and rear electrodes of the ceramic are then manually attached to electrical conductors which enable the transducer to be driven. Next, an acoustic impedance matching layer is cast on the patient face of the disc and an acoustic backing is cast on the rear side of the transducer to absorb undesired acoustic energy emanating from the rear face of the ceramic. The resulting architecture is labor intensive to build and is not well suited for high volume manufacturing.

In accordance with the principles of the present invention, low cost, high volume manufacturing for single element transducers is facilitated by mass processing of materials and assembly as well as by elimination of the transducer housing. The inventive transducer architecture results in a mechanical form conducive to surface mounting on a flexible circuit for efficient electrical termination and connection to an ultrasound system.

In the drawings:

FIGS. 1*a*, 1*b*, and 1*c* illustrate the mass dicing of a piezo ceramic bulk laminate.

Figure 6:
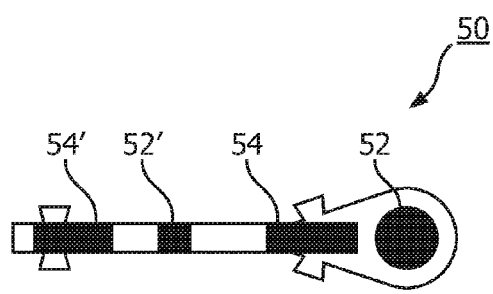
FIG. 6 illustrates flex circuit for mounting one single element transducer.
Figure 7A:
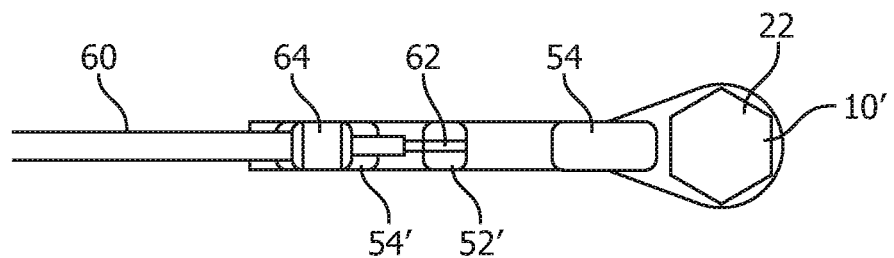
Figure 7B:
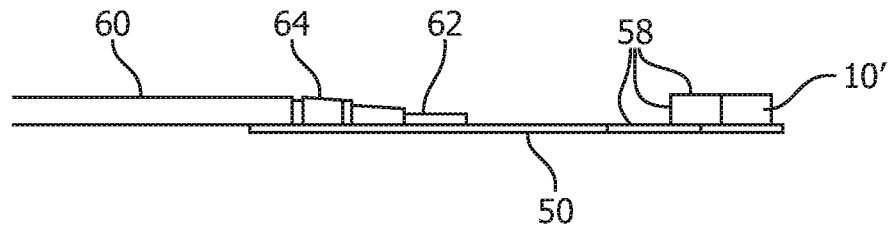

FIGS. 7*a* and 7*b* illustrate a transducer element mounted on the flex circuit of FIG. 6.

Figure 5:
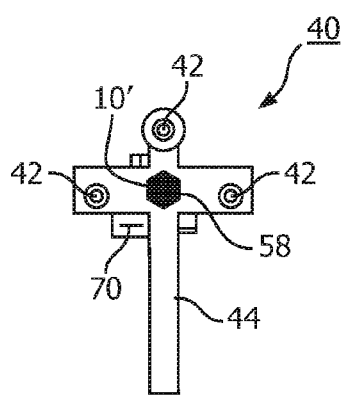
FIG. 5 illustrates flex circuit on which a plurality of single element transducers are mounted.
Figure 8:
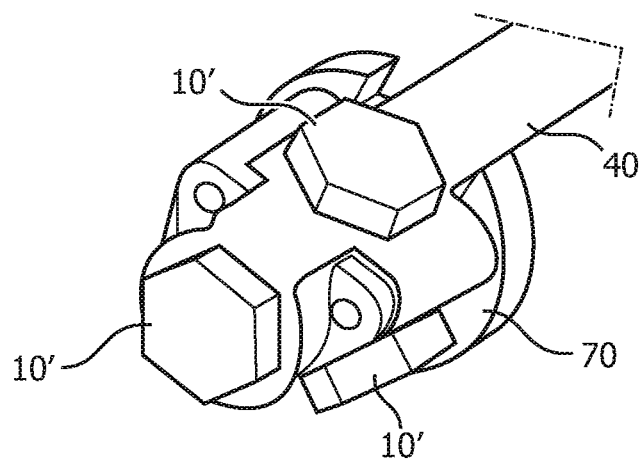

FIG. 8 illustrates the flex circuit mounted transducers of FIG. 5 wrapped around a distal insert for an intravascular catheter.

Figure 9:
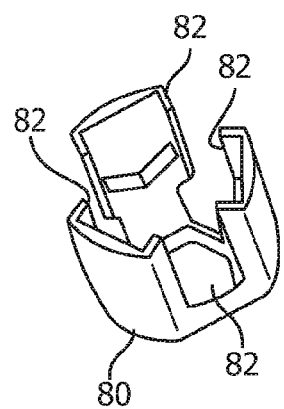

FIG. 9 illustrates an acoustic window for the assembly of FIG. 8.

Figure 10:
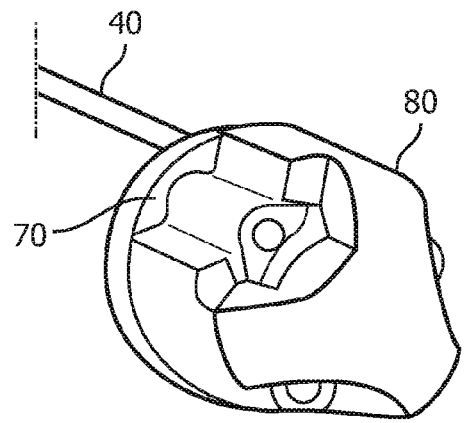

FIG. 10 illustrates the acoustic window of FIG. 9 when mounted over the assembly of FIG. 8.

Figure 11:
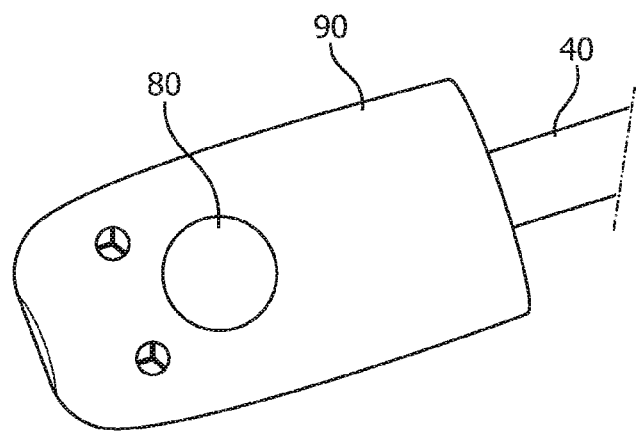

FIG. 11 illustrates the assembly of FIG. 10 when encapsulated in a catheter tip enclosure.

Figure 1A:
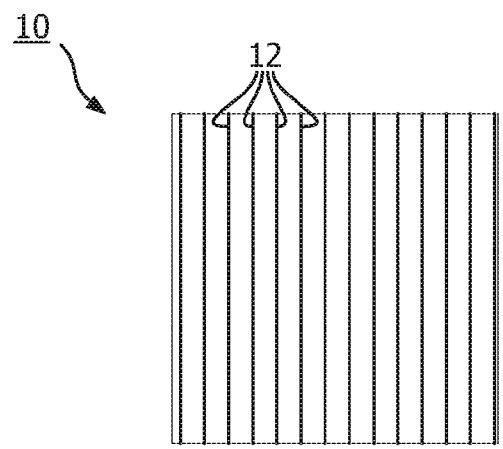
Figure 1B:
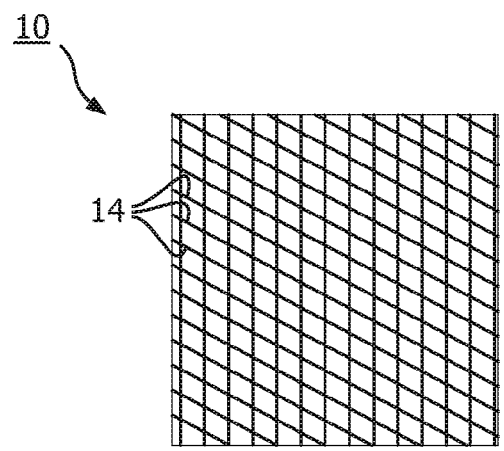
Figure 1C:
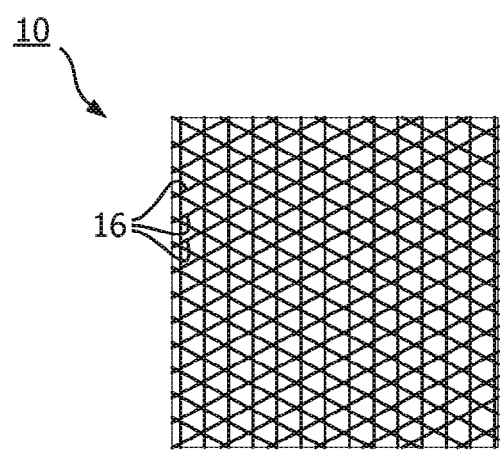

Referring first to FIGS. 1*a*-1*c*, a piezo ceramic bulk laminate 10 is shown which is to be processed to form a plurality of single element transducers. Preparation of the bulk laminate starts with a plate of piezo ceramic which has been ground to the desired thickness for a single element transducer. Front and rear electrodes are then applied to the ceramic plate. An electrically conductive acoustic matching layer is cast on one face of the ceramic plate and ground to the necessary thickness for the desired impedance matching. A conductive backing is cast on the other side of the ceramic plate and ground to a smooth finish. A typical backing is an epoxy in which metallic particles are in suspension. The backing will damp acoustic energy emanating from the rear of the transducer element, aided by the scattering of energy by the suspended particles. An alternate approach is to cast and grind both the matching layer and backing to final thickness as separate parts and then bond them to the ceramic. A metallic layer is then sputtered on the rear surface of the backing to form a signal electrode. The thus-formed bulk laminate 10 is then mounted matching layer side down on nitto tape, a low tack adhesive tape commonly used in semiconductor fabrication.

The bulk laminate 10 which is mounted on the nitto tape is then diced into individual transducer elements as shown in FIGS. 1*a*-1*c*. A first series of parallel dicing cuts 12 are then made through the bulk laminate, extending slightly into the nitto tape to assure cleanly cut sides to the elements as shown in FIG. 1*a*. Next, the bulk laminate is diced by a second series of parallel cuts 14 oriented −60° to the first series of cuts as shown in FIG. 1*b*. Finally, a third series of parallel dicing cuts 16 are made which are oriented +60° to the first series. As a result, the bulk laminate plate 10 is diced into a large number of hexagonal single element transducers still adhered to the nitto tape as FIG. 1*c* illustrates. While the processing of this example forms hexagonal transducer elements, octagonal or square shaped elements may also be diced, or round elements could be cut by core drilling the bulk laminate. Other desired shapes may also be used.

Figure 2:
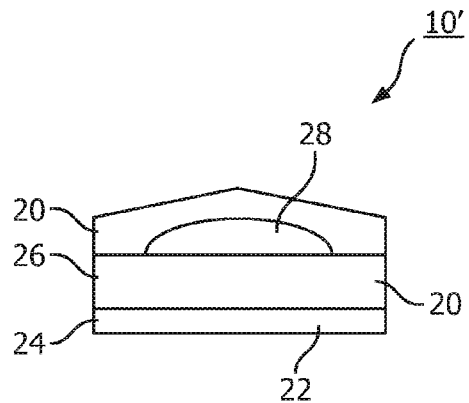
FIGS. 2 and 3 illustrate a single element from the bulk laminate which has been insulated by a parylene coating.
Figure 3:
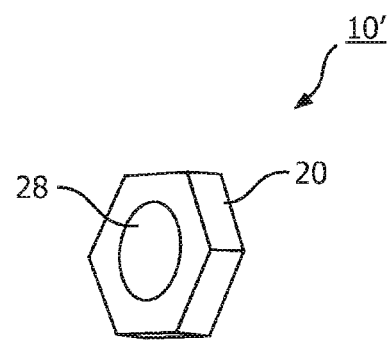

With the singulated elements 10' still mounted on the nitto tape, the sides of the elements are now electrically insulated. This may be accomplished by various techniques. One is to parylene coat the exposed surfaces of the elements by vapor deposition. The parylene coating forms an insulating, high dielectric polymer coating 20 on all surfaces of the elements except for the front surfaces with the matching layer 22, which are masked by being adhesively attached to the nitto tape. The parylene coating 20 on the rear of the elements is then laser ablated to create a window through the parylene which exposes the rear electrode 28 of each element. The laser is also used to sever the parylene coating at the bottom of each kerf to singulate the transducers. Alternatively the rear electrodes can be masked during the deposition process to permit later electrical access to the rear electrodes. An element processed by parylene coating 20 is shown in partial cross-section in FIG. 2, and in perspective in FIG. 3.

Figure 4:
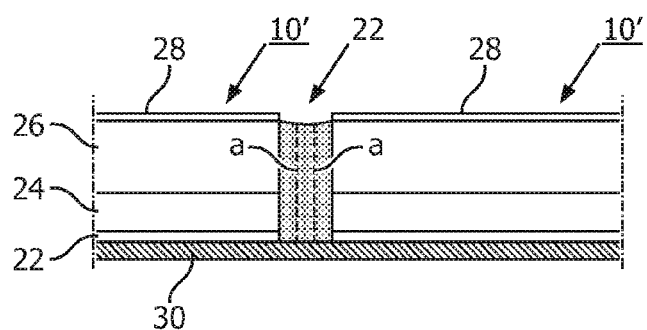
FIG. 4 illustrates epoxy insulation of single element transducers.

Another technique for insulating the sides of the elements is to flood the dicing cuts between the singulated elements with nonconductive epoxy as shown in FIG. 4. This illustration shows a dicing cut 12 between two singulated elements 10' which has been filled with epoxy. The filling is not allowed to spill over the tops of the elements 10' so that the rear electrodes 28 remain exposed for electrical connections. As before, the matching layers 22 on the front faces of the elements 10' are masked from the epoxy by their attachment to the nitto tape 30. After the epoxy has cured, the elements are diced again but now with a thinner dicing saw than was used to dice the ceramic laminate. This dicing separates the singulated elements again with cuts bounded in the center of the epoxy as shown by dashed lines a-a in FIG. 4, which leaves an insulating epoxy coating on the sides of the elements 10'.

The singulated elements are now in condition for surface mounting on flex circuit which couples electrical signals to and from the elements. As is well known, flex circuit comprises a flexible non conductive substrate on which electrically conductive traces, pads and areas have been formed. A flex circuit 40 for mounting four transducer elements 10' is shown in FIG. 5. In this example the lightly shaded areas is conductive material and the more darkly shaded areas is devoid of conductive material. The majority of the area on the visible side of the flex circuit 40 comprises a return conductor 44 which is to be coupled to the conductive matching layers 22 of the mounted elements. The four small circular conductive areas 42, isolated from the return conductor by circular void areas, are electrically coupled to traces on the back side of the flex circuit and are to be coupled to the signal electrodes of the elements. The electrical connection of the signal electrodes 28 of the elements 10' to the signal conductors 42 of the flex circuit 40 are made by picking an element 10' from the nitto tape 30 and bonding it in electrical connectivity to a signal conductor 42 on the flex circuit 40. FIG. 5 shows a transducer element 10' which has been bonded to a signal conductor in the center of the flex circuit. The bonding may be done with a small drop of conductive epoxy or thin bonding with a non conductive epoxy. Three other elements 10' are bonded in similar fashion to the other three signal conductor areas 42.

Electrical connection for signal return to the patient-facing matching layers 22 of the four elements is done by applying metallized electrode material to the exposed (top) faces of the matching layer of each transducer element and down the sides of the previously insulated sides of the elements and onto the surrounding return conductor 44 of the flex circuit. The return conductor 44 thus provides the common electrical return signal path for all of the elements mounted on the flex circuit. The elements are seen to be held in place on the flex circuit by both the rear electrode bonding to the signal conductor areas 42 and the metallized layer laid over all of the elements down to the return conductor 44.

While the flex circuit of FIG. 5 is seen to mount multiple transducer elements, a flex circuit 50 for a single transducer element is shown in FIG. 6. The flex circuit 50 has a signal conductor 52 which is electrically connected to signal lead conductor 52' and a return conductor 54 which is electrically connected to return lead conductor 54', all located on a flexible high dielectric substrate. As before, the signal electrode 28 of a transducer element 10' is bonded in electrical connection with the signal conductor 52 and a metallized layer 58 covers and is in electrical communication with the conductive matching layer 22 on the top (patient facing) side of the element, continues down the insulated sides of the element, and onto the flex circuit and in electrical communication with the return conductor 54 of the flex circuit 50, as shown in FIGS. 7a and 7b. These latter figures are a plan view and a side view of the flex circuit 50 with it mounted transducer element 10' to which a coax line 60 is connected. The braid 64 of the coax which provides the electrical return is electrically bonded to the return lead conductor 54' and the center conductor 62 of the coax which is the signal lead is electrically bonded to the signal lead conductor 52' of the flex circuit 50.

The flex circuit in either implementation may now be assembled with the other components of an ultrasound probe. FIGS. 8-11 illustrate such an assembly for an ultrasonic catheter probe. FIG. 8 shows the flex circuit 40 and its mounted transducer elements 10' wrapped around and bonded to a frame called a distal insert 70 for the tip of a catheter. When the flex circuit is wrapped as shown in this drawing, one transducer element is located in an end-fired position at the very tip of the catheter and the other three transducer elements are positioned for radial transmission and reception every 120° around the periphery of the catheter tip. The adhesive bond between the rear surface of the flex circuit and the distal insert maintains transducer position. The acoustic window 80 shown in FIG. 9 has hexagonal depressions 82 which cover each of the transducer elements. These mating surfaces are adhesively bonded to the face of the corresponding transducers to fix the window in-place and facilitate transmission of acoustic energy. FIG. 10 shows the flex circuit and distal insert 70 after the acoustic window 80 has been bonded to this subassembly. FIG. 11 shows the assembly of FIG. 10 after a tip enclosure 90 has been slipped over it. In this drawing, the acoustic window 80 for one of the radially directed transducer elements is visible on the side of the tip. The assembled acoustic catheter tip is now ready for connection to the rest of the catheter.

What is claimed is:

1. A single element ultrasonic transducer assembly comprising:
   a piezo ceramic element having a front surface, a rear surface and sides and comprising a piezo ceramic layer, a front matching layer, and a rear backing layer;
   an insulating coating formed over the sides of the piezo ceramic element and extending from the front surface to the rear backing layer; and
   a flex circuit on which the piezo ceramic element is surface mounted by electrical bonding of the rear backing layer to a flex circuit signal conductor and electrical bonding of the front matching layer to a flex circuit return conductor.

2. The single element ultrasonic transducer assembly of claim 1, wherein the rear backing layer comprises a signal electrode located on the rear surface.

3. The single element ultrasonic transducer assembly of claim 2, wherein the front matching layer comprises an electrically conductive matching layer.

4. The single element ultrasonic transducer assembly of claim 1, wherein the insulating coating comprises a parylene coating.

5. The single element ultrasonic transducer assembly of claim 4, wherein the insulating coating further comprises a window for electrically accessing the rear backing layer.

6. The single element ultrasonic transducer assembly of claim 1, wherein the insulating coating comprises a coating of non conductive epoxy.

7. The single element ultrasonic transducer assembly of claim 1, wherein the piezo ceramic element is one of a plurality of piezo ceramic elements diced from a piezo ceramic laminate plate.

8. The single element ultrasonic transducer assembly of claim 1, further comprising three additional piezo ceramic elements surface mounted on the flex circuit and arranged so that one piezo ceramic element is positioned as an end-fired single element transducer and the other three piezo ceramic elements are positioned as radially fired single element transducers.

9. The single element ultrasonic transducer assembly of claim 1, further comprising three additional flex circuits on which three additional piezo ceramic elements are mounted, the flex circuits with mounted piezo ceramic elements being positioned so that one is an end-fired single element transducer and the other three piezo ceramic elements are positioned as radially fired single element transducers.

10. The single element ultrasonic transducer assembly of claim 9, wherein the flex circuits with mounted piezo ceramic elements are mounted on a distal insert.

11. The single element ultrasonic transducer assembly of claim 10, wherein the flex circuits and piezo ceramic elements are further covered with an acoustic window.

12. The single element ultrasonic transducer assembly of claim 11 wherein the acoustic window is further covered with a catheter tip enclosure.

13. A catheter comprising the single element ultrasonic transducer assembly of claim 1.

14. The single element ultrasonic transducer assembly of claim 1, further comprising a metallized electrode material on the front matching layer.

15. The single element ultrasonic transducer assembly of claim 1, wherein the piezo ceramic element is connected to a coax line.

* * * * *